(12) United States Patent
Liu et al.

(10) Patent No.: US 10,420,653 B2
(45) Date of Patent: Sep. 24, 2019

(54) FUSION CAGE AND CLAMPING DEVICE THEREOF

(71) Applicant: SHANGHAI SANYOU MEDICAL CO., LTD., Shanghai (CN)

(72) Inventors: Michael Mingyan Liu, Shanghai (CN); Wen Yuan, Shanghai (CN); Jean Charles Lehuec, Shanghai (CN); Xing Liu, Shanghai (CN)

(73) Assignee: SHANGHAI SANYOU MEDICAL CO., LTD., Jiading District, Shanghai (CN)

( * ) Notice: Subject to any disclaimer, the term of this patent is extended or adjusted under 35 U.S.C. 154(b) by 126 days.

(21) Appl. No.: 15/522,292

(22) PCT Filed: Dec. 30, 2014

(86) PCT No.: PCT/CN2014/095459
§ 371 (c)(1),
(2) Date: Apr. 27, 2017

(87) PCT Pub. No.: WO2016/065721
PCT Pub. Date: May 6, 2016

(65) Prior Publication Data
US 2017/0312096 A1 Nov. 2, 2017

(30) Foreign Application Priority Data

Oct. 27, 2014 (CN) .......................... 2014 1 0582037
Oct. 27, 2014 (CN) .................... 2014 2 0626397 U

(51) Int. Cl.
*A61F 2/44* (2006.01)
*A61F 2/46* (2006.01)
(Continued)

(52) U.S. Cl.
CPC ........ *A61F 2/4455* (2013.01); *A61B 17/1728* (2013.01); *A61B 17/7059* (2013.01);
(Continued)

(58) Field of Classification Search
CPC ... A61F 2/4455; A61F 2/4611; A61B 17/7059
See application file for complete search history.

(56) References Cited

U.S. PATENT DOCUMENTS 5,423,855 A * 6/1995 Marienne ........... A61B 17/2833
606/206
2006/0235403 A1 * 10/2006 Blain ................. A61B 17/7059
606/249

(Continued)

FOREIGN PATENT DOCUMENTS

| CN | 1708259 A | 12/2005 |
|---|---|---|
| CN | 101027015 A | 8/2007 |
| CN | 101610741 A | 12/2009 |

*Primary Examiner* — Christian A Sevilla
(74) *Attorney, Agent, or Firm* — Global IP Services; Tianhua Gu

(57) ABSTRACT

Disclosed are a fusion cage for a spinal surgery and a clamping device thereof. The fusion cage comprises a fusion cage body (1) and a triangular screw plate (2). A limiting groove (12) fit with the clamping device is provided at a rear end surface of the fusion cage body (1), the fusion cage body (1) is hinged with the screw plate (2), and each of three corners of the screw plate (2) is provided with a screw hole (23). The clamping device comprises two clamping rods (4) which are fit with each other, and a front end of each clamping rod (4) is provided with a clamping head (41), wherein each of face-to-face sides of the clamping heads (41) is provided with a limiting protrusion (42), a front end of each clamping head (41) is capable of being inserted into the limiting groove (12) of the fusion cage body (1), and the limiting protrusion (42) is capable of being clamped at a front side surface of the screw plate (2). The fusion cage and (Continued)

the clamping device can easily fit with each other and are convenient to use, so as to enable the surgical operation to be more convenient, accurate and safe.

10 Claims, 7 Drawing Sheets

(51) Int. Cl.
  *A61B 17/70* (2006.01)
  *A61F 2/30* (2006.01)
  *A61B 17/17* (2006.01)
  *A61B 17/80* (2006.01)
(52) U.S. Cl.
  CPC .............. *A61B 17/808* (2013.01); *A61F 2/44* (2013.01); *A61F 2/442* (2013.01); *A61F 2/447* (2013.01); *A61F 2/46* (2013.01); *A61F 2/4611* (2013.01); *A61F 2002/30182* (2013.01); *A61F 2002/30428* (2013.01); *A61F 2002/30622* (2013.01); *A61F 2002/4615* (2013.01); *A61F 2002/4622* (2013.01)

(56) References Cited

U.S. PATENT DOCUMENTS

| | | | |
|---|---|---|---|
| 2006/0235405 A1* | 10/2006 | Hawkes | A61B 17/7008 606/70 |
| 2009/0326580 A1* | 12/2009 | Anderson | A61B 17/7059 606/246 |
| 2010/0016968 A1* | 1/2010 | Moore | A61B 17/15 623/17.11 |
| 2011/0190892 A1* | 8/2011 | Kirschman | A61F 2/44 623/17.16 |
| 2012/0130497 A1 | 5/2012 | Taylor | |

* cited by examiner ent application is the US national stage of PCT/CN2014/095459 filed on Dec. 30, 2014, which claims the priorities of the Chinese patent applications No. 201410582037.X filed on Oct. 27, 2014 and 201420626397.0 filed on Oct. 27, 2014, which applications are incorporated herein by reference.

FUSION CAGE AND CLAMPING DEVICE THEREOF

CROSS REFERENCE TO RELATED PATENT APPLICATION

The present application is the US national stage of PCT/CN2014/095459 filed on Dec. 30, 2014, which claims the priorities of the Chinese patent applications No. 201410582037.X filed on Oct. 27, 2014 and 201420626397.0 filed on Oct. 27, 2014, which applications are incorporated herein by reference.

FIELD OF INVENTION

The present invention relates to a spinal medical apparatus, in particular to a fusion cage between spinal vertebrae and a clamping device thereof.

DESCRIPTION OF RELATED ARTS

At present, after a spinal intervertebral disc is excised, usually a titanium network, a fusion cage and a biological material are used for substituting the excised part of the intervertebral disc, and then multi-step internal fixing operations are performed by using a proper screw plate and bone screws. In a surgical process, since the screw plate is fit with a surface of spinal vertebrae and occupies a space of the original part, consequently a secondary damage is inevitably caused to the internal part of a body. However, the volume of the screw plate in the prior art is generally large and the damage to the human body is also great. Besides, the operation steps of the traditional spinal surgery are comparatively tedious and generally comprise: 1) clamping a fusion cage by using a special tool and implanting the fusion cage to a position between adjacent spinal vertebrae; 2) clamping a screw plate by using a special tool, placing the screw plate at a position at which the fusion cage is implanted, and adjusting the position of the fusion cage to guarantee that the fusion cage is not retreated; and 3) drilling holes by using a special tool, screwing in temporary fixing screws, sequentially screwing in and fixing bone screws, and finally fixing the screw plate on the spinal vertebrae.

According to the above-mentioned operation steps, many adverse effects will be produced in the entire operation process, e.g., 1) the screw plate is dislocated or deflected; 2) the screwing and mounting of the bone screws mainly depend on the operation skills of a doctor and deflection is very easily caused; 3) the bone screws cannot be fully sunk into the screw holes of the screw plates, etc. The occurrence of these problems will cause problems such as that the surgery is repeated and reworked, the surgery time is prolonged and the surgery risk is increased in a disguised form. Therefore, a fusion cage which is convenient to use and can be conveniently operated by a doctor and a device which facilitates the mounting of a screw plate are needed.

SUMMARY OF THE PRESENT INVENTION

The technical problem to be solved by the present invention is to provide a fusion cage which is convenient to use and can be stably positioned, so as to overcome the above-mentioned defects of the prior art.

In order to solve the above-mentioned technical problems, the present invention adopts the following technical solution: a fusion cage comprises a fusion cage body and further comprises a triangular screw plate behind the fusion cage body, at least one limiting groove is provided at a rear end surface of the fusion cage body, the limiting groove is fit with a tool for clamping the fusion cage, the fusion cage body is hinged with the screw plate, and each of three corners of the screw plate is provided with a screw hole.

Preferably, the rear end surface of the fusion cage body is provided with a clamping block, the number of the provided limiting grooves is two, the clamping block is located between the two limiting grooves, a front side surface of the screw plate is provided with an upper clamping plate and a lower clamping plate which protrude forwards, a clamping groove is formed between the upper clamping plate and the lower clamping plate, and the clamping groove is in hinging fit with the clamping block of the fusion cage body.

Further, the clamping block of the fusion cage body is of a T-shaped structure or L-shaped structure, the T-shaped structure or L-shaped structure comprises a transverse cylindrical body and a connecting rod which connects the cylindrical body with the fusion cage body, and the cylindrical body is capable of rotating in the clamping groove formed by the upper clamping plate and the lower clamping plate.

Preferably, a middle position of the screw plate is provided with a threaded hole, a locking screw is provided in the threaded hole, and an edge of a cap of the locking screw covers edges of the three screw holes.

Preferably, a top surface and a bottom surface of the fusion cage body are rough curved surfaces.

The present invention further provides a clamping device for clamping the fusion cage and adopts the following technical solution: a clamping screw for clamping the fusion cage comprises two clamping rods which are fit with each other, a front end of each clamping rod is provided with a clamping head, each of face-to-face sides of the clamping heads is provided with a limiting protrusion, a front end of each clamping head is capable of being inserted into a limiting groove of a fusion cage body, and the limiting protrusion is capable of being clamped on a front side surface of the screw plate.

Preferably, the clamping device further comprises a guide seat, three guide holes corresponding to screw holes of the screw plate are provided on the guide seat, the guide seat consists of two halves, and the two halves are respectively provided on two clamping rods and are adjacent to clamping heads.

Preferably, rear ends of the clamping rods are provided with a locking structure, and the locking structure is capable of locking the rear ends of the two clamping rods together.

Further, the locking structure comprises a limiting nut, the limiting nut is mounted at the rear end of one clamping rod, an edge of an end surface, facing to one side of the clamping head, of the limiting nut is provided with an annular protrusion, and the limiting nut is capable of limiting the rear end of the other clamping rod in a space formed by the annular protrusion when the limiting nut is rotated.

Further, the rear end of the clamping rod on which the limiting nut is located is provided with a retaining ring which prevents the limiting nut from getting off.

As described above, the fusion cage and the clamping device thereof provided by the present invention have the following beneficial effects:

1. The fusion cage and the clamping device in the present invention are used in a fit manner; the operations of drilling the holes on the spinal vertebrae and screwing in the bone screws can be realized in one step through the guide seat during a spinal surgery; the clamping device is taken down after the above-mentioned work is completed, the locking screw is screwed in, and thereby the implanting of the fusion cage and the positioning of adjacent vertebrae can be completed. Various adverse events in a conventional surgery are prevented from occurring during use of the present invention. Besides, after the clamping device clamps the fusion cage, the clamping device and the fusion cage become an integral body, and thereby the fusion cage body can be smoothly implanted into the gap between the vertebrae. In addition, the screw plate can swing upwards and downwards for certain angles, and thereby the screw plate and the surface of the vertebrae can be better closely fit together. Therefore, the present invention can enable the surgical operation to be more convenient, accurate and safe.

2. The volume of the triangular screw plate in the present invention is reduced by ¼ relative to the volume of the quadrangular screw plate commonly used in the prior art, and the triangular screw plate can be more easily fit with the surface of the vertebrae.

3. The safety and reliability are high during use of the present invention, the positioning and mounting of the screw plate are performed by using the principle of stability of a triangle, and the triangular screw plate is more safe and reliable than the long-strip-shaped screw plate in the prior art.

Figure 1:
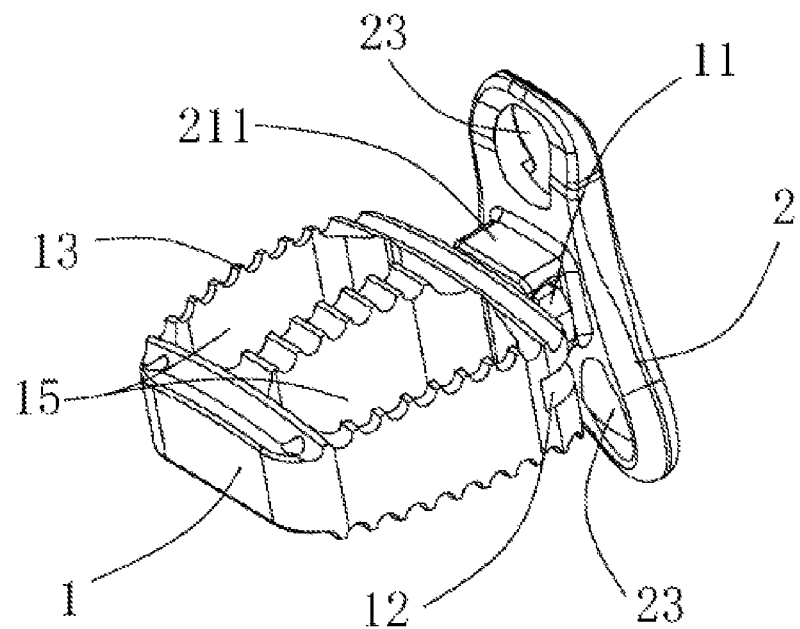
FIG. 1 illustrates a stereoscopic view of a fusion cage in the present invention.

| 1 | Fusion cage body | 11 | Clamping block | 111 | Cylindrical body |
|---|---|---|---|---|---|
| 112 | Connecting rod | 12 | Limiting groove | 13 | Rough curved surface |
| 14 | Bone screw | 15 | Through hole | 16 | Ball socket |
| 2 | Screw plate | 211 | Upper clamping plate | 212 | Lower clamping plate |
| 22 | Clamping groove | 23 | Screw hole | 24 | Threaded hole |
| 25 | Ball head | 3 | Locking screw | 4 | Clamping rod |
| 41 | Clamping head | 42 | Limiting | 43 | Leaf spring |

-continued

| 5 | Limiting nut | 51 | protrusion Annular protrusion | 6 | Guide seat |
|---|---|---|---|---|---|
| 61 | Guide hole | 7 | Retaining ring | 8 | Rotating rod |
| 81 | Toothed bar | 9 | Convex tooth | 100 | Vertebra |

DETAILED DESCRIPTION OF THE PREFERRED EMBODIMENTS

Structures, scales, sizes and the like illustrated in the drawings are only used for cooperating with the contents disclosed by the description for the sake of understanding and reading by one skilled in the art, are not used for limiting the limited conditions that the present invention can be implemented and thus have no technical substantive meanings. Any modification to structures, change to scale relations or adjustment to sizes without influencing the effects which can be produced by the present invention and the purposes which can be achieved by the present invention shall still fall into the range which can be covered by the technical contents disclosed by the present invention. In addition, terms such as "above", "below", "front", "rear" and "middle" used in the description are only used for facilitating the clearness of description and are not used for limiting the range that the present invention can be implemented. Change or adjustment to relative relations without substantively changing the technical contents shall also be considered as the range that the present invention can be implemented.

Figure 2:
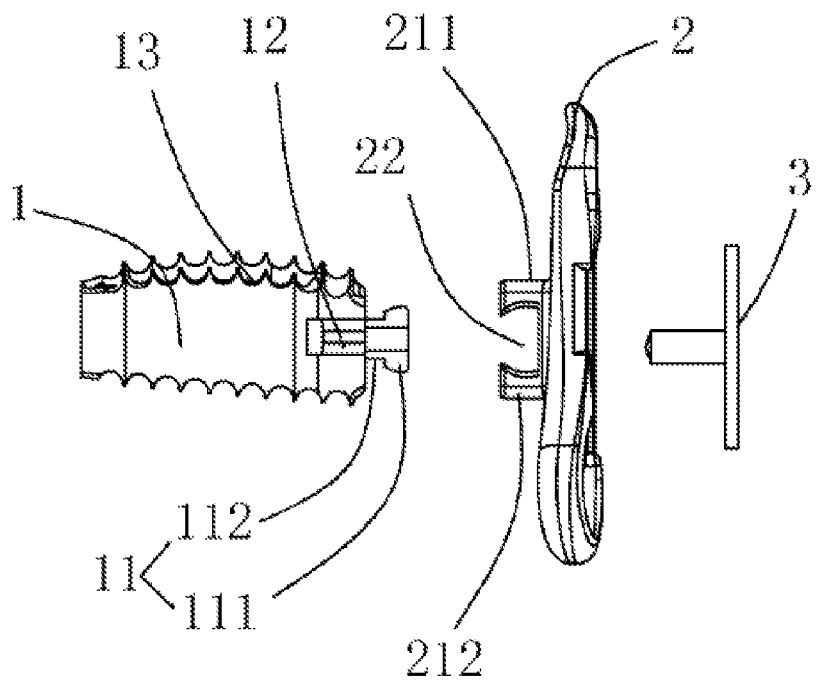
FIG. 2 illustrates a structural view of a fusion cage in a first implementation mode in the present invention.
Figure 3:
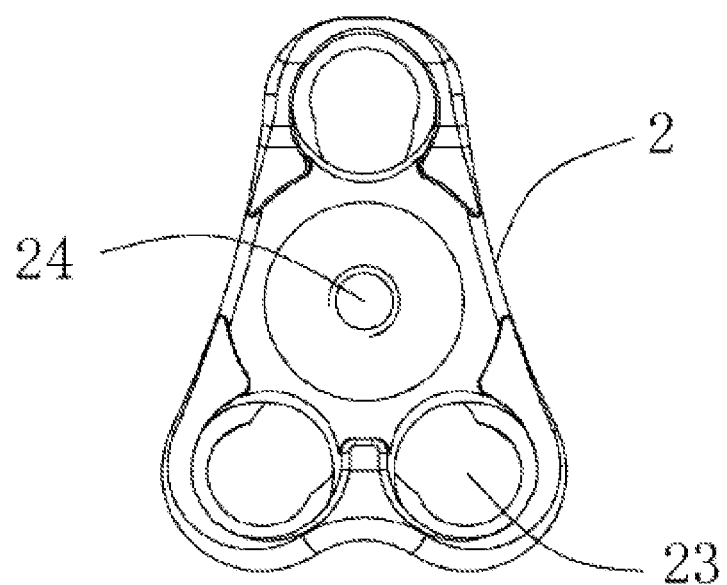
FIG. 3 illustrates a schematic view of a screw plate on a fusion cage in the present invention.

As illustrated in FIG. 1 to FIG. 3, the present invention provides a fusion cage, comprising a fusion cage body 1 and further comprising a triangular screw plate 2 behind the fusion cage body 1, at least one limiting groove 12 is provided at a rear end surface of the fusion cage body 1, the limiting groove 12 is fit with a tool for clamping the fusion cage, the fusion cage body 1 is hinged with the screw plate 2, and each of three corners of the screw plate 2 is provided with a screw hole 23. In the present invention, there are two implementation modes for hinging the fusion cage body 1 with the screw plate 2. A first implementation mode is that, as illustrated in FIG. 1 and FIG. 2, the rear end surface of the fusion cage body 1 is provided with a clamping block 11, the number of the provided limiting grooves 12 is two, the clamping block 11 is located between the two limiting grooves 12, a front side surface of the screw plate 2 is provided with an upper clamping plate 211 and a lower clamping plate 212 which protrude forwards, a clamping groove 22 is formed between the upper clamping plate 211 and the lower clamping plate 212, and the clamping groove 22 is in hinging fit with the clamping block 11 of the fusion cage body 1. A second implementation mode is that, as illustrated in that FIG. 4, the rear end surface of the fusion cage body 1 is provided with a ball socket 16, the number of the provided limiting grooves 12 is two, the two limiting grooves 12 are located at two sides of the ball socket, the front side surface of the screw plate 2 is provided with a protruding ball head 25, and the ball head 25 is in hinging fit with the ball socket 16 of the fusion cage body 1 to achieve the purpose of hinging the fusion cage body 1 with the screw plate 2. In the present invention, the first implementation mode is a preferred solution. By taking the first implementation mode as an example, since the clamping block 11 is in hinging fit with the clamping groove 22, during actual operation, after the fusion cage body 1 is mounted in place, i.e., between adjacent spinal vertebrae, the screw plate 2 can be rotated in an allowable range and thus the screw plate 2 can be better in close fit with the surface of the spinal vertebrae. In the present invention, a plurality of through holes 15 are provided at the fusion cage body 1, the through holes 15 are used for filling with implant bones in a surgical process to facilitate better fusion between the fusion cage body 1 and the spine. Reasons for using the triangular screw plate 2 in the present invention are to, on one hand, guarantee the mounting stability of the screw plate 2 by using the principle of stability of a triangle, and on the other hand, reduce unnecessary occupied spaces in a human body and minimize the secondary damage to the human body since the volume of the triangular screw plate 2 is ¼ smaller than the volume of a traditional quadrangular screw plate. In the present invention, in order to facilitate the fitting with the clamping device for clamping the fusion cage, the limiting groove 12 is communicated with left and right sides of the fusion cage body 1, and the clamping device may be inserted into the limiting grooves 12 from the two sides of the fusion cage body 1 to clamp the fusion cage body 1. In the present invention, the front side surface of the screw plate 2 is a flat surface structure or a curved surface structure. Preferably, in this embodiment, in order to enable the front side surface of the screw plate 2 to be better fit with the spinal vertebrae during a surgery, the front side surface is a smooth curved surface structure. Besides, in order to enable the screw plate 2 to better adapt to tissues in the human body and simultaneously prevent edges and corners of the screw plate 2 from damaging the tissues of the human body, the rear side surface of the screw plate 2 is also a smooth curved surface structure.

In the present invention, the clamping block 11 of the fusion cage body 1 is in hinging fit with the clamping groove 22 of the screw plate 2 to realize an effect that the fusion cage body 1 and the screw plate 2 can rotate relatively. During a spinal surgery, under a general situation, it is not needed that there is a very great relative rotation range between the fusion cage body 1 and the screw plate 2, as long as the fusion cage body 1 and the screw plate 2 can relatively rotate in a fixed range. Therefore, in a preferred solution of this embodiment, in combination with FIG. 1 and FIG. 2, the clamping block 11 of the fusion cage body 1 is of a T-shaped structure or L-shaped structure, the T-shaped structure or L-shaped structure comprises a transverse cylindrical body 111 and a connecting rod 112 which connects the cylindrical body 111 with the fusion cage body 1, the cylindrical body 111 is capable of rotating in the clamping groove 22 formed by the upper clamping plate 211 and the lower clamping plate 212, and the rotation of the cylindrical body 111 can drive the fusion cage body 1 to swing up and down relative to the screw plate 2. When the fusion cage body 1 and the screw plate 2 are fit and mounted, the cylindrical body 111 is inserted into the clamping groove 22 from one side, and this implementation mode can also allow adjustment of the transverse position between the fusion cage body 1 and the screw plate 2.

Figure 13:
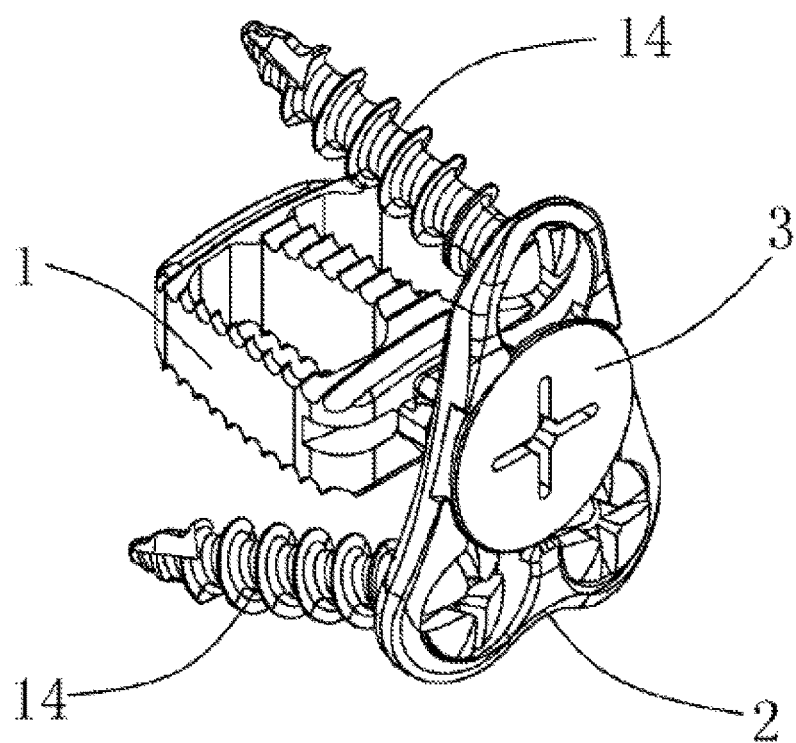
FIG. 13 illustrates a schematic view of a fusion cage in a final use state.

In this embodiment, in order to prevent bone screws mounted in screw holes 23 from getting off during a surgery, as illustrated in FIG. 2, FIG. 3 and FIG. 13, a middle position of the screw plate 2 is provided with a threaded hole 24, a locking screw 3 is provided in the threaded hole 24, and an edge of a cap of the locking screw 3 covers edges of the three screw holes 23. After the bone screws 14 are screwed in the spinal vertebrae, the cap of the locking screw 3 presses against the caps of the bone screws 14 to limit the positions of the bone screws 14 and prevent the bone screws 14 from getting off.

Figure 4:
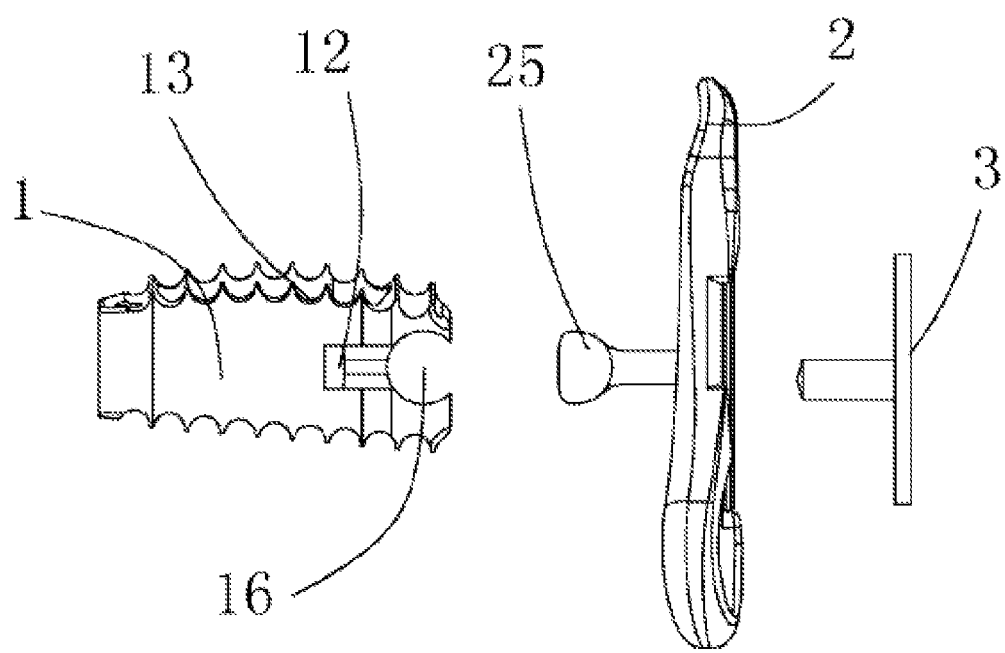
FIG. 4 illustrates a structural view of a fusion cage in a second implementation mode in the present invention.

In an actual surgery, the fusion cage body 1 mounted between the spinal vertebrae may slip. Therefore, in order to avoid this situation, as illustrated in FIG. 1, FIG. 2 or FIG. 4, a top surface and a bottom surface of the fusion cage body 1 are rough curved surfaces 13.

In this embodiment, the number of the provided clamping blocks 11 is two, and the two clamping blocks 11 are transversely arranged in parallel at the rear end of the fusion cage body 11. Further, the two clamping blocks 11 are located on two sides of the middle position of the rear end of the fusion cage body 1, a space between the two clamping blocks is used for holding a rod portion of the locking screw 3, so as to guarantee that the rod portion of the locking screw 3 has enough length and prevent the locking screw 3 from getting off.

Figure 5:
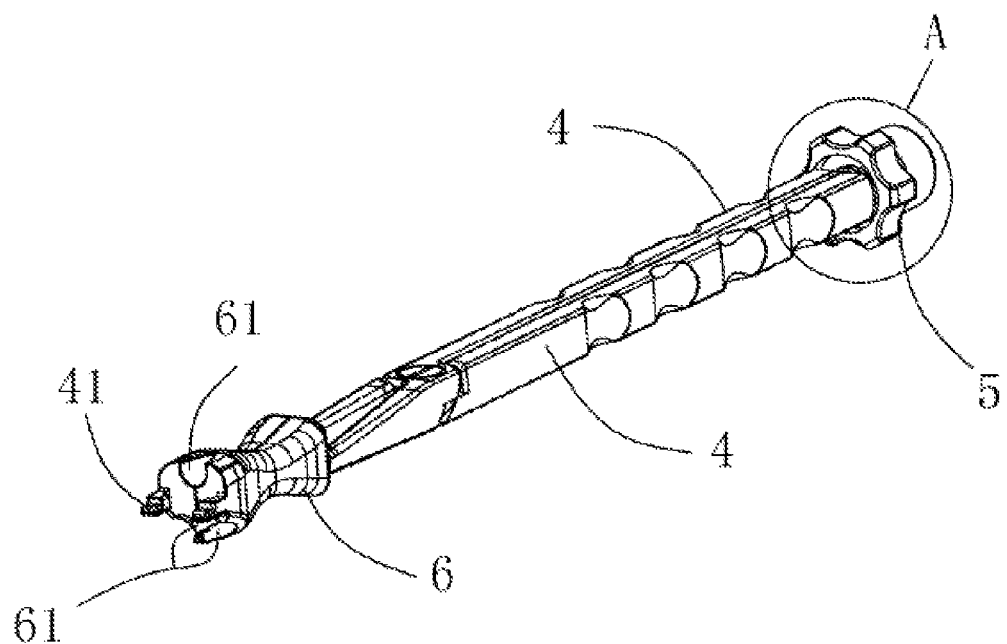
FIG. 5 illustrates a stereoscopic view of a clamping device in the present invention.
Figure 7:
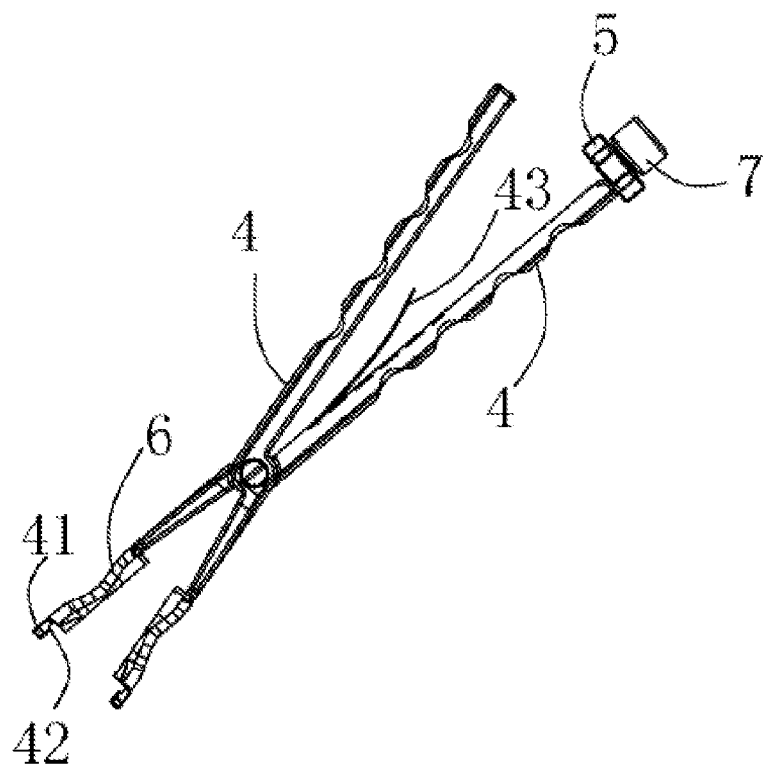
FIG. 7 illustrates a schematic view of a clamping device in an implementation mode in the present invention.
Figure 8:
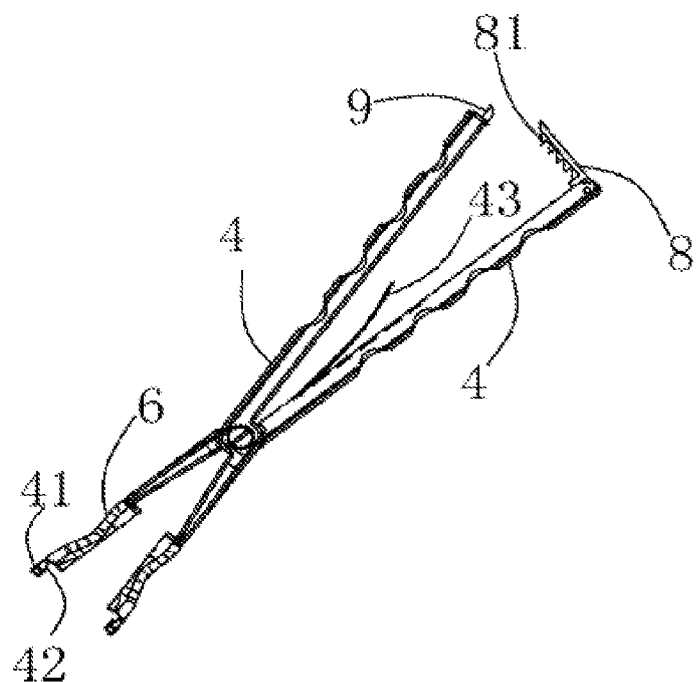
FIG. 8 illustrates a schematic view of a clamping device in another implementation mode in the present invention.

As illustrated in FIG. 5, the present invention further provides a clamping device for clamping the fusion cage, the clamping device comprises two clamping rods 4 which are fit with each other, a front end of each clamping rod 4 is provided with a clamping head 41, each of face-to-face sides of the clamping heads 41 is provided with a limiting protrusion 42, with reference to FIG. 1, a front end of each clamping head 41 is capable of being inserted into a limiting groove 12 of a fusion cage body 1, and the limiting protrusion 42 is capable of being clamped on a front side surface of the screw plate 2. There are various fitting modes for the two clamping rods 4. For example, the two clamping rods 4 are independent, the two clamping rods 4 are aligned and clamp the fusion cage during fitting, and then a sleeve sleeves the two clamping rods 4 to combine the two clamping rods 4 into an integral body. Preferably, in this embodiment, as illustrated in FIG. 7 or FIG. 8, the two clamping rods 4 are hinged together through a rotating shaft to further facilitate the use.

Figure 6:
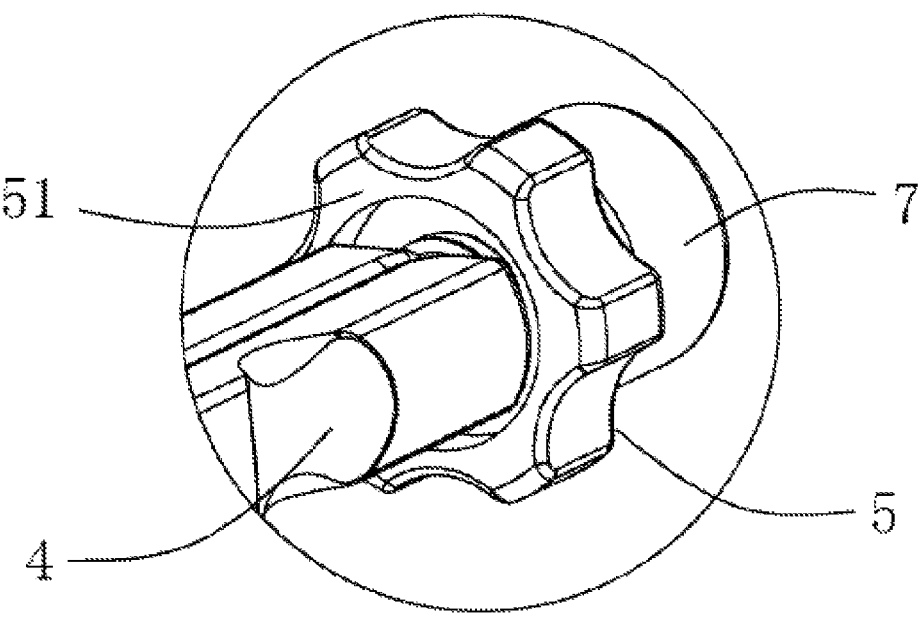
FIG. 6 illustrates an enlarged view of a position A in FIG. 5.

During a surgery, in order to facilitate the operation by a doctor, the rear ends of the clamping rods 4 are provided with a locking structure, the locking structure is capable of locking the rear ends of the two clamping rods 4 together and thereby the doctor does not need to always hold the two clamping rods 4 after the fusion cage body 1 is mounted in the spine. There are various implementation modes for the locking structure. Preferably, in this embodiment, as illustrated in FIG. 5 to FIG. 7, the locking structure comprises a limiting nut 5, the limiting nut 5 is mounted at the rear end of one clamping rod 4 and is in threaded connection with the clamping rod 4, and the limiting nut 5 is capable of moving along a length direction of the clamping rod 4; and an edge of an end surface, facing to one side of the clamping head 41, of the limiting nut 5 is provided with an annular protrusion 51, and the limiting nut 5 is capable of limiting the rear end of the other clamping rod 4 in a space formed by the annular protrusion 51 when the limiting nut 5 is rotated and moves towards one side of the clamping head 41. Besides, the locking structure may also be a structure as illustrated in FIG. 8, wherein the rear end of one clamping rod 4 is hinged with a rotating rod 8, a toothed bar 81 is provided on the rotating rod 8, the rear end of the other clamping rod 4 is provided with convex teeth 9, the toothed bar 81 is fit with the convex teeth 9, and when the convex teeth 9 are clamped on the toothed bar 81, the positions of the two clamping rods 4 are fixed; and when the fusion cage needs to be loosened, the rotating rod 8 is rotated to enabled the toothed bar 81 and the convex teeth 9 to be separated from each other.

Figure 9:
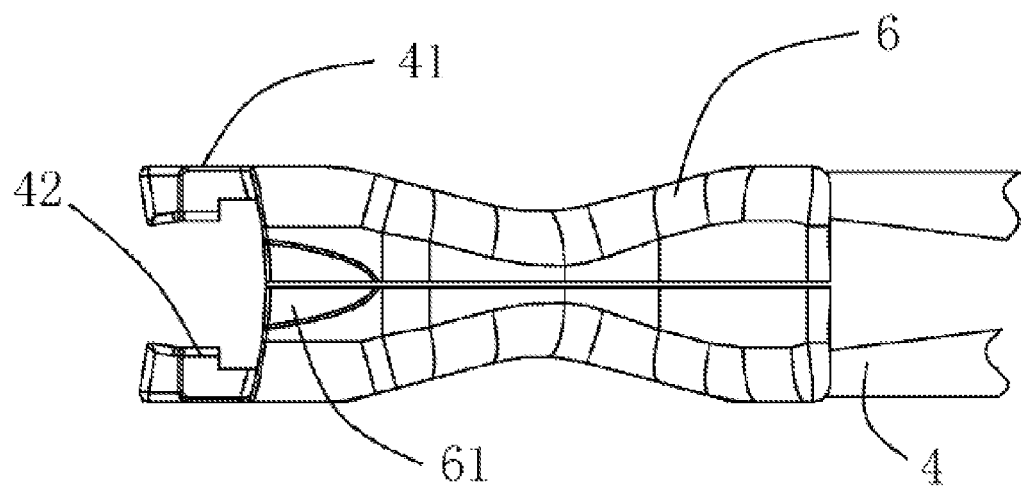
FIG. 9 illustrates a schematic view of a clamping head and a guide seat on a clamping device during fitting in the present invention.
Figure 10:
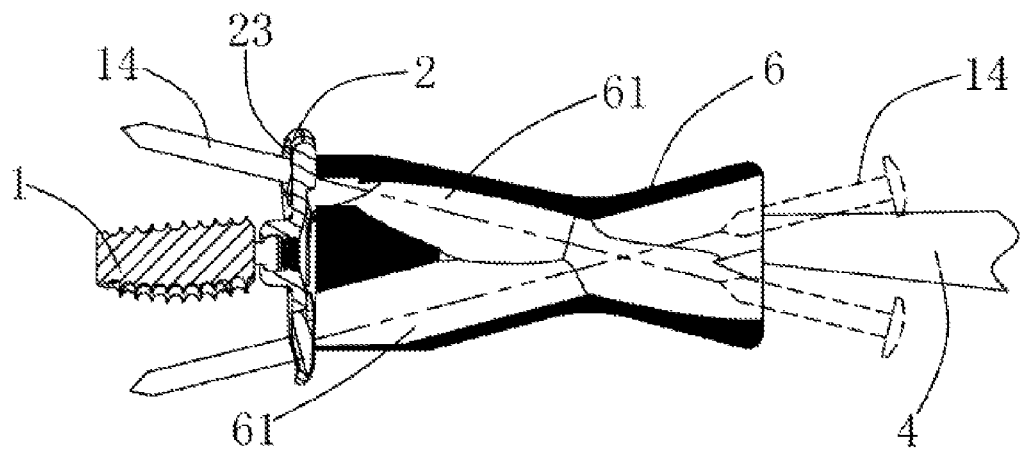
FIG. 10 illustrates a schematic view of bone screws in a mounting mode during use of the present invention.
Figure 11:
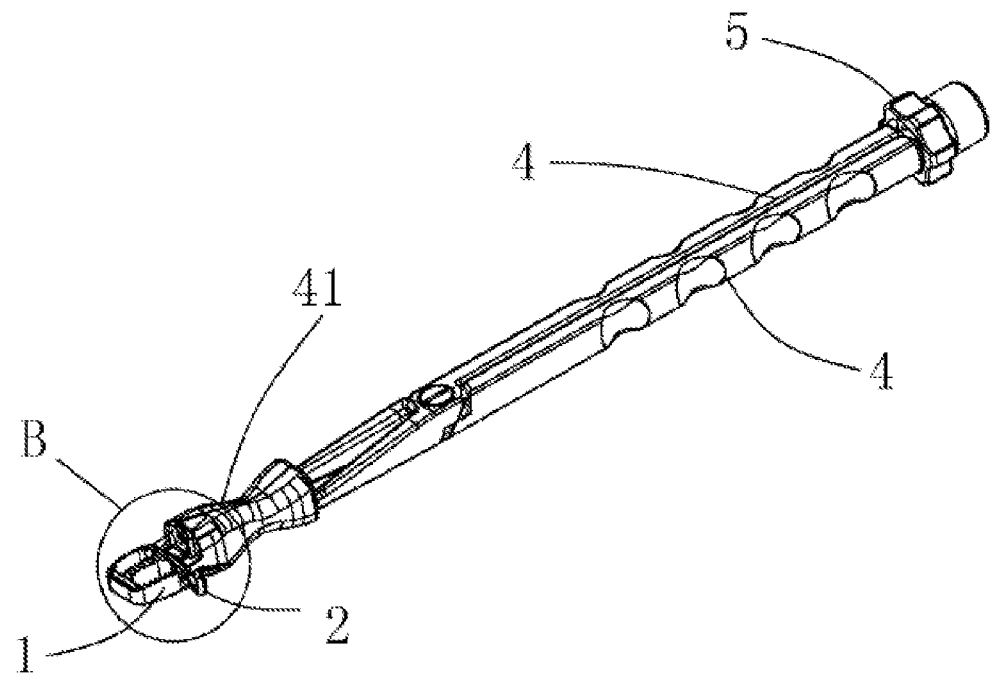
FIG. 11 illustrates a schematic view of a fusion cage and a clamping device during fitting in the present invention.

As illustrated in FIG. 5, FIG. 9 and FIG. 10, the clamping device further comprises a guide seat 6, three guide holes 61 corresponding to screw holes 23 on the screw plate 2 are provided on the guide seat 6, the guide seat 6 consists of two halves, and the two halves are respectively provided on two clamping rods 4 and are adjacent to clamping heads 41. In this embodiment, in order to facilitate the manufacturing, the two halves of the guide seat 6 are the same in structure. In the present invention, the guide holes 61 can guarantee the direction of screwing the bone screws 14 in the vertebrae during a spinal surgery, prevent the bone screws 14 from being dislocation and deflected, thus effectively reduce the surgical difficulty, guarantee the operation accuracy of the surgery and improve the working efficiency. In the present invention, the directions of the guide holes 61 may be determined according to the needs. For example, the directions of the guide holes 61 are the same as the length directions of the clamping rods 4, i.e., the bone screws 14 are enabled to be screwed in the spinal vertebrae in a direction perpendicular to the screw plate 2. Besides, the guide holes 61 may also be obliquely opened, i.e., the bone screws 14 are enabled to be screwed in the spinal vertebrae at a certain angle relative to the screw plate 2. According to actual use, it is found that the effect is the most ideal when the bone screws 14 are obliquely screwed in the spinal vertebrae for positioning. In this state, the bone screws 14 do not get loose and off easily, and the position of the screw plate 2 is stable and is not easily deflected. Preferably, in this embodiment, the guide holes 61 of the guide seat 6 are obliquely opened, i.e., the bone screws 14 are obliquely screwed in the spinal vertebrae. In other words, as illustrated in FIG. 10, when the bone screws are mounted, the bone screws 14 in the screw holes 23 at the upper portion of the screw plate 2 stretch from the guide holes 61 at the lower portion of the guide seat 6, the bone screws in the screw holes 23 at the lower portion of the screw plate 3 stretch from the guide holes 61 at the upper portion of the guide seat 6, and then the bone screws are mounted and tightened.

As illustrated in FIG. 6, the rear end of the clamping rod 4 on which the limiting nut 5 is located is provided with a retaining ring 7, and the retaining ring 7 is capable of preventing the limiting nut 5 from getting off from the clamping rod 4.

In this embodiment, as illustrated in FIG. 7 or FIG. 8, an inner side of one clamping rod 4 is provided with a leaf spring 43 and one end of the leaf spring 43 is fixed on the clamping rod 4. When the locking structure does not lock the positions of the two clamping rods 4, the two clamping rods 4 are sprung apart through the leaf spring 43 such that the doctor can conveniently grasp the fusion cage by using the clamping device.

Figure 12:
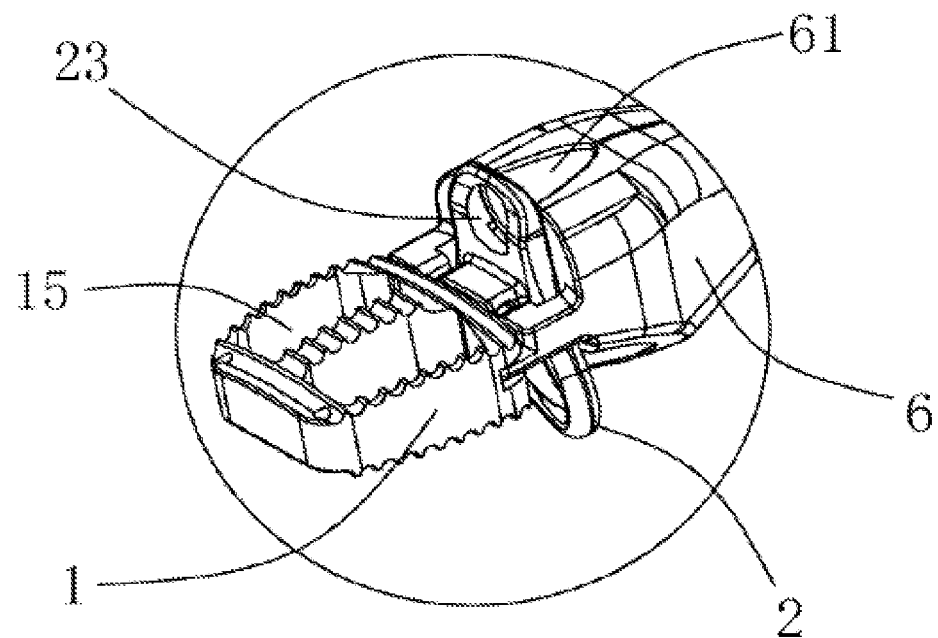
FIG. 12 illustrates an enlarged view of a position B in FIG. 11.
Figure 14:
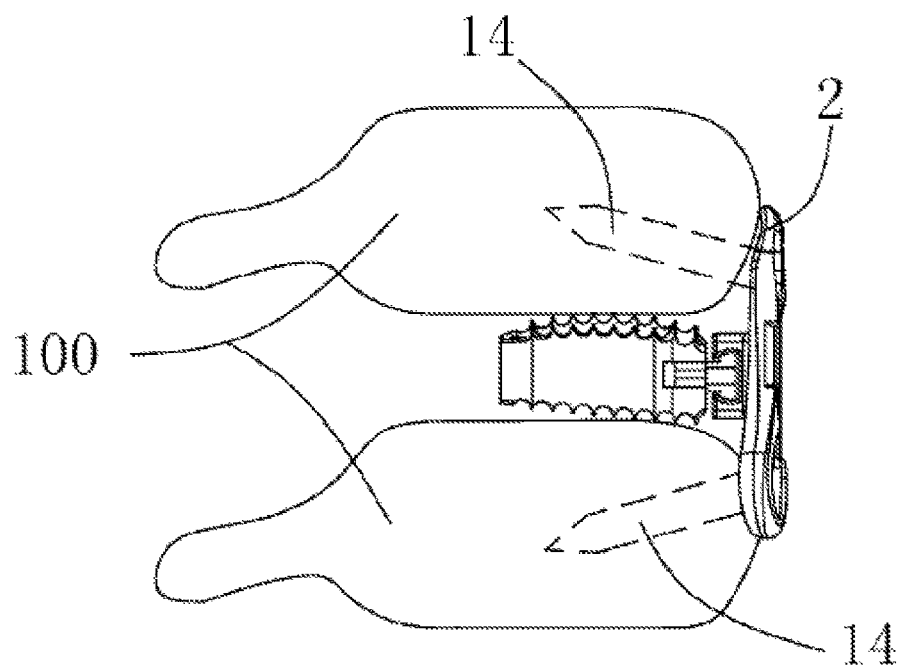
FIG. 14 illustrates an effect view of a fusion cage in a use state.

With reference to FIG. 1 to FIG. 4, the structural principle and the use method of the present invention are as follows:

Firstly, the fusion cage body 1 and the screw plate 2 are fit, the clamping blocks 11 of the fusion cage body 1 are inserted into the clamping groove 22 formed by the upper clamping plate 211 and the lower clamping plate 212, and the two clamping blocks 11 should not block the threaded hole 24 of the screw plate 2. Under a normal state, the two clamping rods 4 of the clamping device are in a separated state. When the fusion cage is clamped, the front ends of the clamping heads 41 are inserted into the limiting grooves 12 of the fusion cage body 1, simultaneously the limiting protrusion 42 is clamped in the front side surface of the screw plate 2, and the screw plate 2 is clamped between the limiting protrusion 42 and the front end surface of the guide seat 6, so as to play a role of clamping the fusion cage, as illustrated in FIG. 12. In a fitting process of the clamping device and the fusion cage, it is required to guarantee that the guide holes 61 of the guide seat 6 are aligned with corresponding screw holes 23 of the screw plate 2. After the clamping device and the fusion cage are fit, the limiting nut 5 on the clamping rod 4 is rotated to lock the positions of the two clamping rods 4, and then the fusion cage can be used in a spinal surgery. During use, the fusion cage body 1 is inserted into a position between two adjacent vertebrae 100 of a spine by using the clamping device. Since the screw plate 2 can swing up and down relative to the fusion cage body 1, the surgical requirements can be better satisfied. After the position of the fusion cage body 1 is determined, the bone screws 14 are delivered through the guide holes 61 of the guide seat 6 and the bone screws 14 are screwed in the vertebrae. After the bone screws 14 are screwed, the limiting nut 5 is rotated, the two clamping rods 4 are enabled to be separated under the effect of the leaf spring 43, then the clamping device is retracted, finally the locking screw 3 is screwed in the threaded hole 24 of the screw plate 2 to further limit the bone screws 14 and prevent the bone screws 14 from getting off, as illustrated in FIG. 13 and FIG. 14, which illustrate a use state of the fusion cage which is finally mounted on the spine.

To sum up, the fusion cage and the clamping device thereof provided by the present invention can solve the problems that the fusion cage is inconvenient to place, the screw plate and the vertebrae cannot be closely fit and the like in the spinal surgery. Therefore, the present invention effectively overcomes some actual problems in the prior art and thus has a very great utilization value and use significance.

The above-mentioned implementation modes are just used for exemplarily describing the principle and effects of the present invention instead of limiting the present invention. The present invention may be improved in various aspects without going against the general thought. One skilled in the art may make modifications or changes to the above-mentioned embodiments without going against the spirit and range of the present invention. Therefore, all equivalent modifications or changes made by those who have common knowledge in the art without departing from the spirit and technical thought disclosed by the present invention shall be still covered by the claims of the present invention.

What is claimed is:

1. A fusion cage, comprising a fusion cage body, further comprising a triangular screw plate behind the fusion cage body, at least one limiting groove for fitting with a tool of clamping the fusion cage is provided at a rear end surface of the fusion cage body, the fusion cage body is hinged with the screw plate, and each of three corners of the screw plate is provided with a screw hole.

2. The fusion cage according to claim 1, wherein, the rear end surface of the fusion cage body is provided with a clamping block, the number of the limiting grooves is two, the clamping block is located between the two limiting grooves, a front side surface of the screw plate is provided with an upper clamping plate and a lower clamping plate which protrude forwards, a clamping groove is formed between the upper clamping plate and the lower clamping plate, and the clamping groove is in hinging fit with the clamping block of the fusion cage body.

3. The fusion cage according to claim 2, wherein, the clamping block of the fusion cage body comprises a transverse cylindrical body and a connecting rod which connects the cylindrical body with the fusion cage body, and the cylindrical body is capable of rotating in the clamping groove formed by the upper clamping plate and the lower clamping plate.

4. The fusion cage according to claim 1, wherein, a middle position of the screw plate is provided with a threaded hole, a locking screw is provided in the threaded hole, and an edge of a cap of the locking screw covers edges of the three screw holes.

5. The fusion cage according to claim 1, wherein, a top surface and a bottom surface of the fusion cage body are rough curved surfaces.

6. A clamping device for clamping the fusion cage according to claim 1, wherein, the clamping device comprises two clamping rods which are fit with each other, a front end of each clamping rod is provided with a clamping head, each of face-to-face sides of the clamping heads is provided with a limiting protrusion, a front end of each clamping head is capable of being inserted into a limiting groove of a fusion cage body, and the limiting protrusion is capable of being clamped at a front side surface of the screw plate.

7. The clamping device for clamping the fusion cage according to claim 6, wherein, the clamping device further comprises a guide seat, three guide holes corresponding to screw holes on the screw plate are provided on the guide seat, the guide seat consists of two halves, and the two halves are respectively provided on two clamping rods and are adjacent to clamping heads.

8. The clamping device for clamping the fusion cage according to claim 6, wherein, rear ends of the clamping rods are provided with a locking structure and the locking structure is capable of locking the rear ends of the two clamping rods together.

9. The clamping device for clamping the fusion cage according to claim 8, wherein, the locking structure comprises a limiting nut, the limiting nut is mounted at the rear end of one clamping rod, an edge of an end surface, facing to one side of the clamping head, of the limiting nut is provided with an annular protrusion, and the limiting nut is capable of limiting the rear end of the other clamping rod in a space formed by the annular protrusion when the limiting nut is rotated.

10. The clamping device for clamping the fusion cage according to claim 9, wherein, the rear end of the clamping rod on which the limiting nut is located is provided with a retaining ring which prevents the limiting nut from getting off.

\* \* \* \* \*